United States Patent [19]

Cheung

[11] 4,224,023

[45] Sep. 23, 1980

[54] DENTAL RESTORATIVE KIT AND METHOD OF RESTORING TOOTH STRUCTURE

[75] Inventor: Peter P. L. Cheung, Gulph Mills, Pa.

[73] Assignee: Pennwalt Corporation, Philadelphia, Pa.

[21] Appl. No.: 714,553

[22] Filed: Aug. 16, 1976

[51] Int. Cl.³ .............................................. A61K 5/06
[52] U.S. Cl. ................................ 433/216; 260/42.15; 260/42.28; 260/42.52; 260/998.11; 433/228
[58] Field of Search ............. 260/42.28, 998.11, 42.15, 260/42.52; 32/15; 433/216, 228

[56] References Cited

U.S. PATENT DOCUMENTS

| | | | |
|---|---|---|---|
| 3,066,112 | 11/1962 | Bowen | 260/42.15 |
| 3,200,142 | 8/1965 | Bowen | 260/309 |
| 3,539,533 | 11/1970 | Lee | 106/35 |
| 3,740,850 | 6/1973 | Bowen | 260/998.11 |
| 3,751,399 | 8/1973 | Lee | 260/998.11 |

*Primary Examiner*—James H. Derrington

[57] ABSTRACT

A non-carious erosion lesion of the cervical region of a tooth is restored without prior drilling preparation by etching the surface of the tooth, applying a primer thereto and filling said lesion with a composite material.

3 Claims, No Drawings

DENTAL RESTORATIVE KIT AND METHOD OF RESTORING TOOTH STRUCTURE

BACKGROUND OF THE INVENTION

1. Field of the Invention

This invention is directed to a dental restorative kit for restoring tooth structure. This invention is also directed to a method of restoring tooth structure without prior drilling preparation thereof.

2. Description of the Prior Art

In the past the restoring of non-carious lesions of the cervical region of teeth required normal cavity preparation to provide retention angles before the placement of the restoration. This procedure made it necessary to remove additional tooth structure at the risk of further weakening the tooth. At present this is the accepted procedure for the restoration of these lesions. Sometimes, this cavity preparation is unnecessary such as where detective but otherwise non-carious enamel is to be restored or where exposed cementum is to be protected. In the latter case, a cavity preparation might cause severe sensitivity or irritation of the pulpal areas.

The instant invention overcome the above mentioned disadvantages of the prior art because the composite adheres to tooth structure without first preparing a cavity.

Prior art dental restoring compositions have been reported in the following United States patents:

| | |
|---|---|
| 3,066,112 | 3,815,239 |
| 3,452,437 | 3,925,895 |
| 3,539,533 | 3,926,906 |
| 3,751,399 | 3,931,678 |
| 3,792,531 | |

SUMMARY OF THE INVENTION

A. A dental restoration kit comprising:
 (a) a particulate solid system of
  (i) 95 to 105 of a fine, silane treated glass,
  (ii) 0.1 to 2 parts of fine silica,
  (iii) 0.5 to 2.5 parts of benzoyl peroxide, and
  (iv) traces of iron oxide pigment as needed for matching the color of tooth structure.
 (b) a liquid binder system of:
  (i) 45 to 65 parts of bisphenol-A/glycidyl methacrylate prepolymer,
  (ii) 5 to 25 parts of hydroxyethyl methacrylate
  (iii) 15 to 45 parts of ethyleneglycol dimethacrylate,
  (iv) 0.001 to 3 parts of methacrylic acid,
  (v) 0.03 to 0.2 parts of p-methoxyphenol, and
  (vi) 0.05 to 1 parts of N,N-dihydroxyethyl-p-toluidine;
 (c) an etching solution of 25 to 50 percent of phosphoric acid; and
 (d) a primer solution of 2 percent N-phenyl glycine/glycidyl methacrylate condensation product in ethanol B. A method of restoring a non-carious erosion lesion of the cervical region of a tooth comprising
 (a) conditioning the surface of the tooth with a 25 to 50 percent solution of phosphoric acid, rinsing and drying the tooth;
 (b) applying a primer solution of 2 percent N-phenyl glycine/glycidyl methacrylate condensation product in ethanol to the tooth to obtain retention to dentin or cementum areas of the tooth;
 (c) filling said lesion with a freshly mixed dental filling composition of
  (1) a particulate solid system of
   (i) 95 to 105 parts of a fine silane treated glass
   (ii) 0.1 to 2 parts of fine silica,
   (iii) 0.5 to 2.5 parts of benzoyl peroxide, and
   (iv) traces of iron oxide pigment as, needed for matching color of tooth structure;
  (2) a liquid binder system of
   (i) 45 to 65 parts of bisphenol-A/glycidyl methacrylate prepolymer,
   (ii) 5 to 25 parts of hydroxyethyl methacrylate
   (iii) 15 to 45 parts of ethyleneglycol dimethacrylate,
   (iv) 0.001 to 3 parts of methacrylic acid
   (v) 0.03 to 0.2 parts of p-methoxyphenol, and
   (vi) 0.05 to 1 parts of N,N-dihydroxyethyl-p-toluidine;
 (d) permitting said composition to harden sufficiently on said tooth.
 (e) finishing said composition on said tooth until said composition matches the original tooth contour.

DETAILED DESCRIPTION OF INVENTION

A method has now been discovered of restoring Class V (gum line) type of lesions without first preparing a cavity in the tooth. The method of the instant invention requires an acid etching of the cervical erosion lesion washing the etched area with water, drying, applying the primer (solution N-phenyl glycine/glycidyl methacrylate condensation product in ethanol), and then flowing into place the composite material to restore the missing tooth structure. The intended use of the invention is to restore areas of gingival erosion (especially moderate and deep erosions) to their normal contours and color.

The composite system of the instant invention has many advantages over the prior art:

(1) The application of the composite system does not require cavity preparation in the tooth structure;

(2) The composite system is flowable, adheres to tooth structure, provides excellent marginal adaptation, and seals the tooth surface to be restored;

(3) Although the composition is not recommended for biting surfaces, it has a sufficiently high compressive strength to withstand oral stresses;

(4) The composition coating on the tooth is stable in the oral environment;

(5) Unused portions of the composite system have excellent shelf stability;

(6) The composition is non-abrasive to metal mixing spatulas; and (7) The composition contains a glass filler to provide a suitable opacity for hiding the background of the area to be restored while providing abrasion resistance; yet, it is easy to polish.

ACID ETCHING

Collected data indicate that 2 mm of dentin exists between the surface of a non-carious lesion of the cercival region of the tooth and the pulp. When the dentin of a tooth is exposed as a result of cervical erosion, changes occur on or in the dentin. Scanning election micrographs indicate that the eroded surface is irregular and contains many small round elevations. The dentinal tubules are completely filled with inorganic matter although a few have openings of various sizes. The rod-like solid deposits in the dentinal tubules protect the pulp during the erosion process and during the acid etch step. When the surface of the tooth is etched, the intertubular dentin is preferentially decalcified and the tubules are accentuated. The tubule openings appear larger. Acid etching cleans the surface of the dentin, enlarges the tubules and possibly opens the dead tracts. Acid etching of enamel, on the other hand, produces a significant increase in enemel porosity. The composite can flow into these pores and ultimately polymerize to produce a mechanical bond that aids in the retention of the materail. The etching solution is a 25 to 50 percent solution of phosphoric acid.

THE PRIMER

The primer is a 2 percent by weight solution of an adduct derived from the reaction of glycidyl methacrylate and N-phenylglycine (called NPG-GMA). The monomer was initially synthesized by Dr. Ray Bowen at the National Bureau of Standards (see U.S. Pat. No. 3,200,142). The monomer is capable of chelating with the calcium ions on the etched surfaces of the tooth and of copolymerizing with the composite material made by mixing the catalyst powder with the universal liquid.

THE COMPOSITE

The composite is composed of a universal liquid and a catalyst powder. The catalyst powder contains a silane treated opaque glass or quartz filler with a mean particle size in the range of 4 to 10 microns with the preferred range being 4 to 7 microns, fine silica, benzoyl peroxide catalyst and iron oxide pigments to produce shade variations to match most tooth enamel. The glass or quartz is the filler material for the composite system. The Silane treated quartz or glass filler must have a suitable opacity when used in the composite, such that it is capable of hiding defective tooth color and yet has enough translucency to simulate tooth structure. The glass of this invention has the following composition range:
1. 30-45 parts of quarts,
2. 20-30 parts of aluminum oxide,
3. 10-20 parts of cryolite,
4. 4-10 parts of aluminum phosphate, and
5. 10-20 parts of fluorspar.

The silane treatment increases the bonding between the glass and the binder. Although both glass and quartz can be used in the composition, glass is preferred to quartz because glass is softer and can be polished more easily. The amount of glass or quartz in the composite should be in the range of 95 to 105 parts. The fine silica in the composite helps to uniformly disperse the powder ingredients during mixing of the composite. The fine silica should be in the range of 0.1 to 2.0 parts. The benzoyl peroxide (called BPO) is the polymerization initiator and should be present in the composite in the range of 0.5 to 2.5 parts. The pigments are used in trace amounts as needed for matching the various colors of tooth structure.

The universal liquid contains the viscous monomer, Bisphenol A/glycidyl methacrylate prepolymer (called BIS-GMA), various diluting monomers, stabilizers and an amine accelerator. The BIS-GMA is the organic binder and should be present in the composite in the range of 45 to 65 parts. Hydroxyethyl methacrylate (called HEMA) is a diluting monomer for copolymerizing with the BIS-GMA to provide better adhesion of the polymer to the glass and tooth structure; HEMA should be present in the composite in the range from 5 to 25 parts. Ethylene glycol dimethacrylate (called EGDMA) is also a diluting monomer for crosslinking and copolymerizing with BIS-GMA and HEMA; EGDMA should be present in the composite in the range of 15 to 45 parts. Methacrylic acid (called MAA) insures a quick final set of the composite after mixing the powder and liquid systems. The MAA should be in the composite from 0.001 to 3 parts. P-Methoxyphenol is a stabilizer in the composite that provides shelf stability of the monomers in the presence of the initiator and controls the working time. Other similar stabilizers may also be used. P-Methoxyphenol is also known as methyl ether hydroquinone (called MEHQ) and should be present in the amount of 0.03 to 0.2 parts. N,N-Dihydroxyethyl-p-toluidine (called DHET) or dimethly-p-toluidine (called DMT) is a co-catalyst I (or accelerator) with the BPO for the polymerization; this ingredient should be present in the amount of 0.05 to 1 part. In order for the composite to harden, the catalyst powder must be mixed with the universal liquid.

EXAMPLES I to III

TABLE A

| Powder | I | II | III |
|---|---|---|---|
| Glass (silane treated) | 100 parts | 100 parts | 100 parts |
| Fine Silica | 0.1 | 0.1 | 0.1 |
| Benzoyl Peroxide | 1.2 | 1.2 | 1.2 |
| Iron Oxide Pigment | trace | trace | trace |
| Liquid | | | |
| BIS-GMA | 56 parts | 56 parts | 56 parts |
| HEMA | 15 | 10 | 25 |
| EGDMA | 28 | 23 | 28 |
| MAA | 0.5 | 0.5 | 0.5 |
| MEHQ | 0.06 | 0.06 | 0.06 |
| DHET | 0.1 | 0.05 | 0.1 |

The compositions shown in Table A are specific examples of formulations used in the composite kit. The directions for use of the kit are as follows: The tooth surface to be restored is clean with fluoride free and oil-free pumice. The tooth color is matched to one of three shade guide tabs present in the kit. Based on the shade guide number on the tab a composite catalyst powder which will provide the desired shade is selected. The tooth is etched with a 25 to 50% solution of phosphoric acid for about one or two minutes. The tooth is then washed with water and dried with oil-free air. For restoring eroded gingival areas, a 2% ethanol solution of N-phenyl glycine/glycidyl methacrylate condensation product should be applied. The treated tooth surface should then be again blown dry. Next a fluid paste is prepared (having a composition such as shown in Examples I to III in Table A) by mixing 0.07 parts liquid with 0.14 parts powder and is applied to the missing tooth structure. The material begins to set within two minutes and sets hard within five minutes from the start of mixing. Generally, no polishing is necessary. The restoration is rinsed with water to remove the unpolymerized surface layer. Nevertheless, additional finishing, if desired, may be accomplished with conventional discs after the hardening of the material.

PROPERTIES OF THE COMPOSITE

Adhesion Testing

A qualitative test has been designed to determine whether the composite sticks to tooth structure. A thermal cycling machine was designed to cycle test specimens between two baths. One bath is maintained at 5° C. and the other at 55° C. The temperature range represents the possible extremes found in the mouth e.g. drinking a cold beverage or a hot beverage. Each cycle consists of 10 seconds in cold water, 5 seconds in air and 10 seconds in hot water. A dye is placed in each bath to detect leakage under the restoration.

The specimen preparation requires that the cementum area of the test tooth be cleaned, acid etched, primed and coated with the composite. The tooth is subjected to 1500 cycles on the thermal cycling machine. At the end of the test, the restorative material is knocked off the tooth and the surface under the restorative is examined for dye penetration.

A comparison between cementum areas coated with another composite and with the composite of this invention revealed that cementum areas coated with the other composite lost their restorations after 500 cycles. The cementum areas coated with the composite of this invention did not show any evidence of dye penetration under the restoration when the composite restoration was removed at the end of 1500 cycles. It may be concluded that the composite adheres to the cementum. In a clinical study it was observed that a high percentage of cervical erosion lesions treated in the manner described in this invention were successfully restored.

Clinical Data

The results are summarized in the Table B entitled "Status of Restorative by Individual Teeth". The evaluations were made using the criteria of the United States Public Health Service. At the base line examination 100 percent of the restorations examined were present, at 6 months, 94.2 percent of the restorations examined were present and at 12 months, 93.8 percent of the restorations were present. The above data indicates that when deep cervical erosion lesions are restored with the composite of the invention, the retention rate is very high.

The composite of the invention was also evaluated for color match, marginal discoloration, anatomical form, marginal adaptation and caries. The results indicated the following:

(a) In most cases the restoration matched the tooth structure (rated A) or the color match was not outside the normal range of tooth color (rated B).
(b) In most cases no discoloration occurred in the margin between the composite and tooth structure (rated A) and if discoloration occured it did not penetrate along the margin of the restorative in a pulpal direction (rated B).
(c) In most cases the composite was not discontinuous with existing anatomic form (rated A) nor was sufficient restorative missing so as to expose dentin (rated B).
(d) In almost every case there was no visible evidence of a crevice along the margin into which the explorer could penetrate (rated A).
(e) No evidence of caries was observed (rated A).

TABLE B

| | \multicolumn{9}{c}{STATUS OF RESTORATIVE BY INDIVIDUAL TEETH} | |
| | Present | Missing | Color Match A | B | Discoloration A | B | Anatomical Form A | B | Marginal Adaptation A | B | Caries A | Total # Teeth Examined |
|---|---|---|---|---|---|---|---|---|---|---|---|---|
| Base Line | 90 | 0 | 52 | 38 | 89 | 1 | 89 | 1 | 90 | 0 | 90 | 90 |
| 6 Months | 66 | 4 | 27 | 39 | 66 | 0 | 66 | 0 | 65 | 1 | 66 | 70 |
| 12 Months | 61 | 4 | 40 | 21 | 56 | 5 | 60 | 1 | 60 | 1 | 61 | 65 |

Toxicity Testing

Samples of the NPG-GMA monomer, the catalyst powder and the universal liquid were placed into several toxicity test procedures using, in general, the "Recommended Standard Practices for Biological Evaluation of Dental Materials", JADA, 84, 382 (1972). The results of these tests indicate that the polymerized materials were found to be non-toxic by mucous membrane test, implantation test and by the oral systemic toxicity test.

What is claimed is:

1. A dental restoration kit for a dentist to use in restoring a non carious erosion lesion of the cervical region of a tooth, said kit being composed of a particulate solid system, a liquid binder system, an etching solution and a primer, all disposed in separate containers, from each of which containers, a dentist may extract necessary amounts of the materials to produce a dental filling to be made, the quantity of material used to produce the filling will match the color of the tooth in which it is to be placed,
    (a) the particulate solid system adapted to be mixed with
    (b) for forming the filling material is composed of
        (i) 95 to 105 parts of a fine silane treated glass,
        (ii) 0.1 to 2 parts of fine silica,
        (iii) 0.5 to 2.5 parts of benzoyl peroxide, and
        (iv) traces of iron oxide pigment as needed for matching the color of tooth structure; and
    (b) the liquid binder system adapted to be mixed with
        (a) for forming the filling material is composed of
            (i) 45 to 65 parts of bisphenol-A/glycidyl methacrylate prepolymer,
            (ii) 5 to 25 parts of hydroxyethyl methacrylate
            (iii) 15 to 45 parts of ethyleneglycol dimethacrylate,
            (iv) 0.001 to 3 parts of methacrylic acid,
            (v) 0.03 to 0.2 parts of p-methoxyphenol, and
            (vi) 0.05 to 1 parts of N,N-dihydroxyethyl-p-toluidine.
    (c) an etching solution of 25 to 50 percent of phosphoric acid adapted to be applied to the tooth for preparing the surface thereof; and
    (d) a primer solution of 2 percent N-phenyl glycine/glycidyl methacrylate condensation product in ethanol adapted to be applied to the tooth for forming a bond therewith by chelating with the calcium ions on the etched surfaces of the tooth and copolymerizing with the filling material.

2. The dental restoration kit of claim 1 wherein the particulate solid system is:
 (i) 100 parts of fine, silane treated glass,
 (ii) 0.1 parts of fine silica,
 (iii) 1.2 parts of benzoyl peroxide, and
 (iv) a trace of an iron oxide pigment having a color selected from the group consisting of red, yellow and black; and the liquid binder system is
 (i) 56 parts of bisphenol-A/glycidyl methacrylate prepolymer
 (ii) 15 parts of hydroxyethyl methacrylate,
 (iii) 28 parts of ethyleneglycol dimethacrylate,
 (iv) 0.5 parts of methacrylic acid,
 (v) 0.06 parts of p-methoxyphenol, and
 (vi) 0.6 parts of N,N-dihydroxyethyl-p-toluidine.

3. The dental restoration kit of claim 1 wherein the glass onto which the silane is treated has the following composition:
 (1) 30–45 parts of quartz,
 (2) 20–30 parts of aluminum oxide,
 (3) 10–20 parts of cryolite,
 (4) 4–10 parts of aluminum phosphate, and
 (5) 10–20 parts of fluorspar.

* * * * *